United States Patent
Purkayastha et al.

(10) Patent No.: US 10,281,468 B2
(45) Date of Patent: May 7, 2019

(54) MICROBIAL IDENTIFICATION AND QUANTITATION USING MS CLEAVABLE TAGS

(71) Applicant: DH Technologies Development Pte. Ltd., Singapore (SG)

(72) Inventors: Subhasish Purkayastha, Acton, MA (US); Subhakar Dey, Lexington, MA (US)

(73) Assignee: DH Technologies Development Pte. Ltd., Singapore (SG)

( * ) Notice: Subject to any disclaimer, the term of this patent is extended or adjusted under 35 U.S.C. 154(b) by 201 days.

(21) Appl. No.: 15/118,850

(22) PCT Filed: Feb. 25, 2015

(86) PCT No.: PCT/IB2015/000232
§ 371 (c)(1),
(2) Date: Aug. 12, 2016

(87) PCT Pub. No.: WO2015/128723
PCT Pub. Date: Sep. 3, 2015

(65) Prior Publication Data
US 2017/0052180 A1    Feb. 23, 2017

Related U.S. Application Data

(60) Provisional application No. 61/946,070, filed on Feb. 28, 2014.

(51) Int. Cl.
| | |
|---|---|
| G01N 33/569 | (2006.01) |
| G01N 30/88 | (2006.01) |
| C12Q 1/04 | (2006.01) |
| C12Q 1/02 | (2006.01) |
| C12Q 1/68 | (2018.01) |
| G01N 30/72 | (2006.01) |
| C12Q 1/686 | (2018.01) |
| G01N 33/68 | (2006.01) |

(52) U.S. Cl.
CPC .............. *G01N 33/569* (2013.01); *C12Q 1/02* (2013.01); *C12Q 1/04* (2013.01); *C12Q 1/68* (2013.01); *C12Q 1/686* (2013.01); *G01N 30/72* (2013.01); *G01N 30/7233* (2013.01); *G01N 30/88* (2013.01); *G01N 33/6848* (2013.01); *G01N 2030/8831* (2013.01)

(58) Field of Classification Search
None
See application file for complete search history.

(56) References Cited

U.S. PATENT DOCUMENTS

| | | | |
|---|---|---|---|
| 6,566,055 B1 | 5/2003 | Monforte et al. | |
| 6,635,452 B1* | 10/2003 | Monforte | C12Q 1/37 435/6.12 |
| 2006/0216760 A1* | 9/2006 | Dieterich | C07K 7/06 435/7.5 |
| 2006/0243900 A1 | 11/2006 | Overney et al. | |
| 2007/0207555 A1* | 9/2007 | Guerra | C07B 59/008 436/518 |
| 2011/0111513 A1 | 5/2011 | Baumann et al. | |
| 2011/0143951 A1* | 6/2011 | Thompson | C12Q 1/6816 506/7 |
| 2016/0370277 A1* | 12/2016 | Winnik | G01N 33/6848 |

OTHER PUBLICATIONS

Belcum et al. Journal of Clinical Microbiology p. 1513-1517, 2012.*
Kitteringhann et al. Journal of Chromatography B, 877, 1229-1239, 2009.*
International Search Report and Written Opinion for PCT/IB2015/000232, dated May 29, 2015.
Pichler et al. "Peptide Labeling with Isobaric Rags Yields Higher Identification Rates Using iTRA! 4-plex Compared to TMT 6-Plex and iTRAQ 8-plex on LTQ Orbitrap," Analytical Chemistry, Aug. 1, 2010, vol. 82, No. 15, Pases 6549-6558.

* cited by examiner

*Primary Examiner* — Michael L Borin
(74) *Attorney, Agent, or Firm* — John R. Kasha; Kelly L. Kasha; Kasha Law LLC

(57) ABSTRACT

Systems and methods are provided for microbial identification using cleavable tags. Control information is sent to a mass spectrometer to select a peptide labeled with a first tag of a known microbe, fragment the labeled peptide of the known microbe, and monitor for an intensity of the first tag in an MRM method using a processor. An ion source provides a beam of ions from a sample that includes peptides labeled with the first tag. The first tag binds to a peptide of a known microbe and is cleaved from the peptide of the known microbe during mass spectrometry. The mass spectrometer receives the beam of ions and is adapted to perform the MRM method on the beam of ions. If the intensity of the first tag received from the mass spectrometer exceeds a threshold value, the known microbe is identified in the sample using the processor.

7 Claims, 11 Drawing Sheets

MICROBIAL IDENTIFICATION AND QUANTITATION USING MS CLEAVABLE TAGS

CROSS REFERENCE TO RELATED APPLICATION

This application claims the benefit of U.S. Provisional Patent Application Ser. No. 61/946,070, filed Feb. 28, 2014, the content of which is incorporated by reference herein in its entirety.

INTRODUCTION

Current mass spectrometry (MS) based approaches for microbial identification employ protein, based or nucleic acid based workflows. In one exemplary protein based workflow provided by Bruker Corporation, microbes are identified from a cultured colony by matching a protein fingerprint obtained on a matrix-assisted laser desorption/ionization (MALDI)-time-of-flight (TOF) platform against a dedicated database of known patterns. In another exemplary protein based workflow provided by Shimadzu and Biomerieux, microbial identification is achieved by obtaining spectra using MALDI-TOF and analyzing the spectra with a MS database. The peaks from the spectra are compared to the characteristic pattern for a species, genus, or family of microorganism.

Unfortunately, however, in a MALDI based workflow, a great variety of experimental conditions, including the laser wavelength, the pulse energy and length, the matrix and co-matrix, and the sample preparation method can have an influence on the ionization process. The same bacteria can give different mass spectra owing to the different culturing conditions or extraction methods. Even though the ribosomal proteins are highly conserved there are differences at the sub-species and strain levels making identification difficult.

In one exemplary nucleic acid based workflow provided by Abbott Laboratories, nucleic acid is extracted from a sample of interest followed by traditional polymerase chain reaction (PCR) amplification of the sequence regions specific to the organism of interest. Upon accurate mass calculation by MS the base composition of number of A, C, G, T bases from the mass of each amplicon is determined, followed by performing a database search against a library to determine and report the organism present. In another exemplary nucleic acid based workflow provided by Agilent Technologies, Inc., individual small molecule MS tags are attached to deoxyribonucleic acid (DNA) primers that correspond to a microbial sequence. The primers are used to amplify nucleic acid using PCR. The PCR step uses two distinctly different tags attached to two primers (forward and reverse) specific for each target DNA or complementary DNA (cDNA). The tags are released by applying ultraviolet (UV) irradiation followed by identification of the tags by MS.

Unfortunately, however, PCR based approaches require exquisitely clean reagents that are free from bacterial and fungal DNA along with workflow process that could lead to contamination. In addition, conventional MS tags have to be released by UV light before MS analysis, because the tags are distinct and chemically different from each other.

SUMMARY

A system is disclosed for microbial identification using cleavable tags that bind to peptides. The system includes an ion source, a mass spectrometer, and a processor that is in communication with the mass spectrometer and the ion source.

The ion source provides a beam of ions from a sample that includes peptides labeled with a first tag that binds to a peptide of a known microbe and is cleaved from the peptide of the known microbe during mass spectrometry. The mass spectrometer receives the beam of ions and is adapted to perform a multiple reaction monitoring (MRM) method on the beam of ions. The processor sends control information to the mass spectrometer to select the labeled peptide of the known microbe, fragment the labeled peptide of the known microbe, and monitor for an intensity of the first tag in the MRM method. If the intensity of the first tag received from the mass spectrometer exceeds a threshold value, the processor identifies the known microbe in the sample.

A method is disclosed for microbial identification using cleavable tags that bind to peptides. Control information is sent to a mass spectrometer to select a peptide labeled with a first tag of a known microbe, fragment the labeled peptide of the known microbe, and monitor for an intensity of the first tag in an MRM method using a processor. An ion source provides a beam of ions from a sample that includes peptides labeled with the first tag. The first tag binds to a peptide of a known microbe and is cleaved from the peptide of the known microbe during mass spectrometry. The mass spectrometer receives the beam of ions and is adapted to perform the MRM method on the beam of ions. If the intensity of the first tag received from the mass spectrometer exceeds a threshold value, the known microbe is identified in the sample using the processor.

A computer program product is disclosed that includes a non-transitory and tangible computer-readable storage medium whose contents include a program with instructions being executed on a processor so as to perform a method for microbial identification using cleavable tags that bind to peptides. The method includes providing a system, wherein the system comprises one or more distinct software modules, and wherein the distinct software modules comprise a control module and an analysis module.

The control module sends control information to a mass spectrometer to select a peptide labeled with a first tag of a known microbe, fragment the labeled peptide of the known microbe and monitor for an intensity of the first tag in an MRM method. An ion source provides a beam of ions from a sample that includes peptides labeled with the first tag. The first tag binds to a peptide of a known microbe and is cleaved from the peptide of the known microbe during mass spectrometry. The mass spectrometer receives the beam of ions and is adapted to perform the MRM method on the beam of ions. If the intensity of the first tag received from the mass spectrometer exceeds a threshold value, the analysis module identifies the known microbe in the sample.

A system is disclosed for microbial identification using cleavable tags that bind to nucleic acids. The system includes an ion source, a mass spectrometer, and a processor that is in communication with the mass spectrometer and the ion source.

The ion source provides a beam of ions from a polymerase chain reaction (PCR) amplified sample that includes one or more nucleic acid primers labeled with a first tag that binds to one or more nucleic acid primers of a known microbe and is cleaved from the one or more nucleic acid primers of the known microbe during mass spectrometry. The mass spectrometer receives the beam of ions and is adapted to perform a mass spectrometry (MS) method on the beam of ions. The processor sends control information to the mass spectrometer to fragment the labeled one or more nucleic acid primers and monitor for an intensity of the first tag in the MS method. If the intensity of the first tag received from the mass spectrometer exceeds a threshold value, the processor identifies the known microbe in the sample.

A method is disclosed for microbial identification using cleavable tags that bind to nucleic acids. Control information is sent to a mass spectrometer to fragment one or more nucleic acid primers labeled with a first tag and monitor for an intensity of the first tag in an MS method using a processor. An ion source provides a beam of ions from a PCR amplified sample that includes one or more nucleic acid primers labeled with the first tag. The first tag binds to one or more nucleic acid primers of a known microbe and is cleaved from the one or more nucleic acid primers of the known microbe during the MS method. The mass spectrometer receives the beam of ions and is adapted to perform the MS method on the beam of ions. If the intensity of the first tag received from the mass spectrometer exceeds a threshold value, the known microbe is identified in the sample using the processor.

A computer program product is disclosed that includes a non-transitory and tangible computer-readable storage medium whose contents include a program with instructions being executed on a processor so as to perform a method for microbial identification using cleavable tags that bind to nucleic acids. The method includes providing a system, wherein the system comprises one or more distinct software modules, and wherein the distinct software modules comprise a control module and an analysis module.

The control module sends control information to a mass spectrometer to fragment one or more nucleic acid primers labeled with a first tag and monitor for an intensity of the first tag in an MS method. An ion source provides a beam of ions from a PCR amplified sample that includes one or more nucleic acid primers labeled with the first tag. The first tag binds to one or more nucleic acid primers of a known microbe and is cleaved from the one or more nucleic acid primers of the known microbe during the MS method. The mass spectrometer receives the beam of ions and is adapted to perform the MS method on the beam of ions. If the intensity of the first tag received from the mass spectrometer exceeds a threshold value, the analysis module identifies the known microbe in the sample.

BRIEF DESCRIPTION OF THE DRAWINGS

The skilled artisan will understand that the drawings, described below, are for illustration purposes only. The drawings are not intended to limit the scope of the present teachings in any way.

Figure 1:
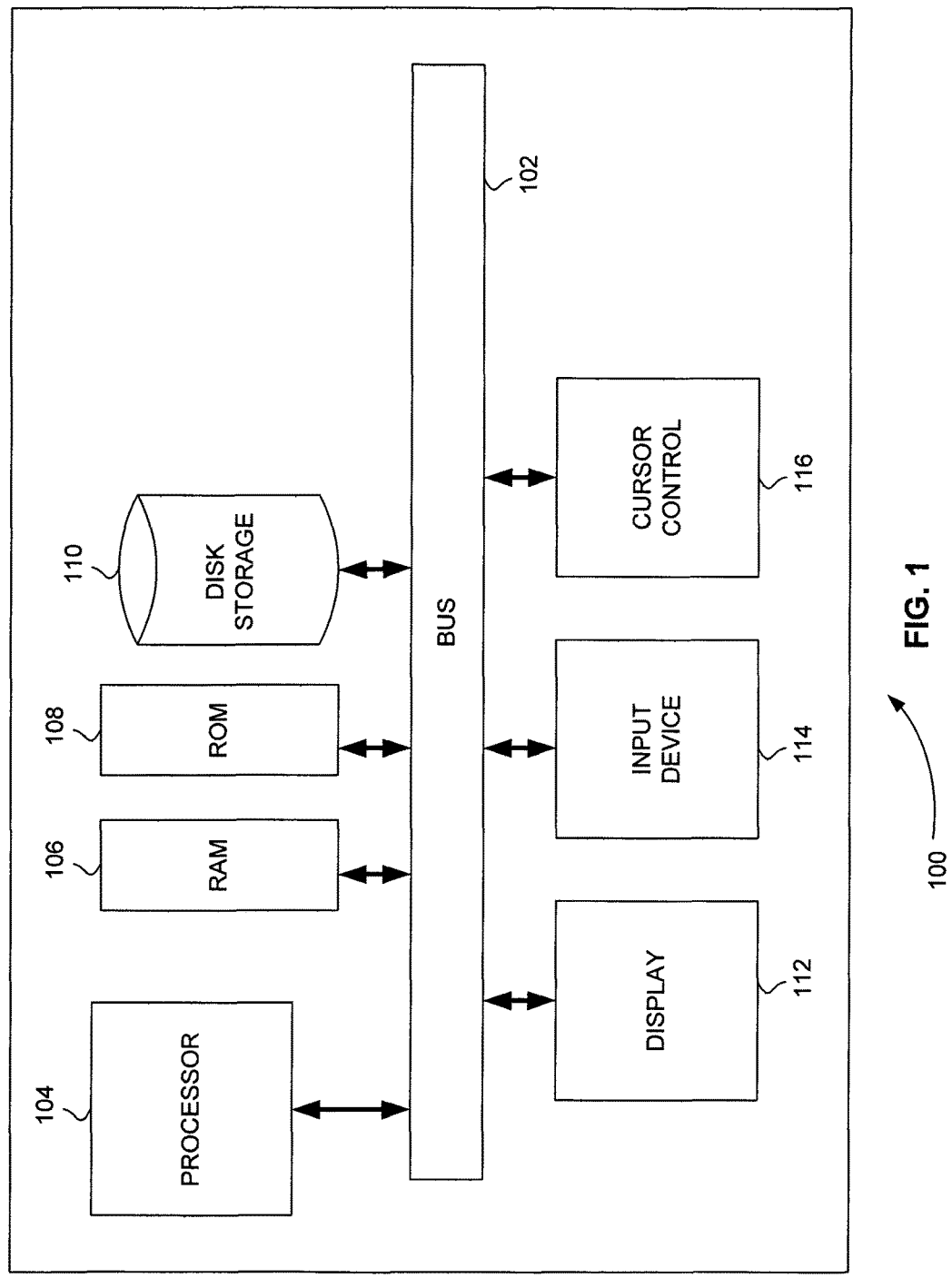
FIG. 1 is a block diagram that illustrates a computer system, upon which embodiments of the present teachings may be implemented.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Systems and Methods for Microbial Identification

As described above, current mass spectrometry (MS) based approaches for microbial identification employ protein based or nucleic acid based workflows. However, in conventional protein based workflows a variety of experimental conditions, including the laser wavelength, the pulse energy and length, the matrix and co-matrix, and the sample preparation method can have an influence on the ionization process. The same bacteria can give different mass spectra owing to the different culturing conditions or extraction methods. Even though the ribosomal proteins are highly conserved there are differences at the sub-species and strain levels making identification difficult.

Similarly, however, in conventional nucleic acid based workflows, clean reagents are required that are free from bacterial and fungal DNA along in order to prevent contamination. In addition, conventional MS tags have to be released by UV light before MS analysis, because the tags are distinct and chemically different from each other.

In various embodiments, methods and systems are provided for microbial identification and quantitation using novel MS cleavable tags and peptide-multiple reaction monitoring (MRM) workflow or nucleic acid-polymerase chain reaction (PCR) based workflow. These methods and systems provide workflows that address some of the problems associated with conventional protein based and nucleic acid based workflows. These methods and systems provide a simple, specific and sensitive method that offers the potential to identify differences at the sub-species and strain levels with confidence. These methods and systems also provide quantitative assessment of pathogen load, which is not provided by current proteome profiling approaches.

In various embodiments, methods and systems provide an MRM, a selected reaction monitoring (SRM), or a liquid chromatography-mass spectrometry/mass spectrometry (LC-MSMS) workflow that is a targeted workflow that targets the detection of pre-determined unique signature peptides specific to the protein(s) that are unique to a microbe of interest. MRM, SRM, or LC-MSMS are described herein for illustration purposes only. One skilled in the art will appreciate that other types of mass spectrometry methods can equally be applied.

Figure 2:
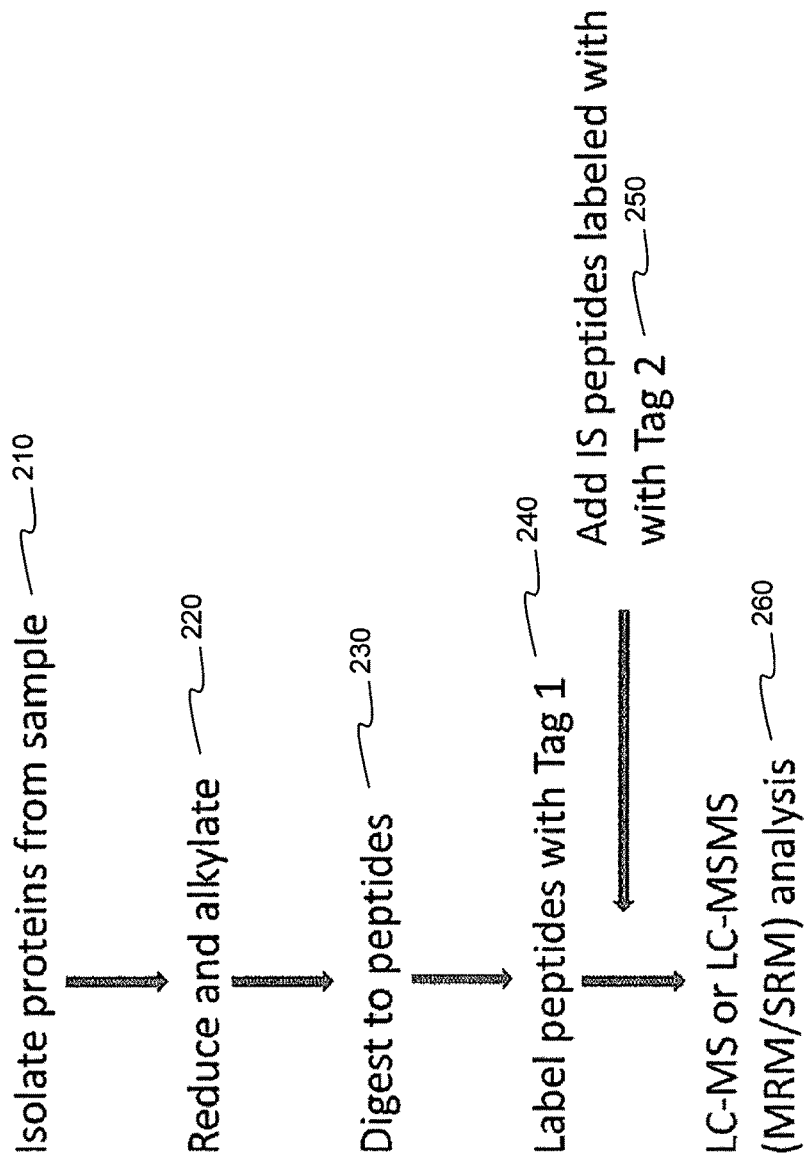
FIG. 2 is a flowchart showing an exemplary peptide based workflow, in accordance with various embodiments.

FIG. 2 is a flowchart showing an exemplary peptide based workflow 200, in accordance with various embodiments.

In step 210 of workflow 200, proteins are isolated from a sample.

In step 220, the isolated proteins are reduced and alkylated.

In step 230, the reduced and alkylated proteins are digested to produce peptides.

In step 240, the peptides are tagged with a first set of tags that bind to one or more peptides of one or more known microbes.

In step 250, proteins of the one or more known microbes are digested on a computer, or in-silico (IS), and the resulting peptides are synthesized. The synthesized peptides are labeled with a second set of tags. Known quantities of one or more synthesized peptides labeled with the second set of tags are then added to the sample containing the peptides with the first tag.

In step 260, MRM or SRM analysis is performed on the sample that includes the peptides with the first tag and the synthesized peptides labeled with the second tag. A microbe is identified by detecting one or more tags from the first set of tags. The microbe is further quantified by comparing the intensities of the one or more detected tags with the intensities of one or more tags from the second set of tags that identify the same microbe.

Figure 3:
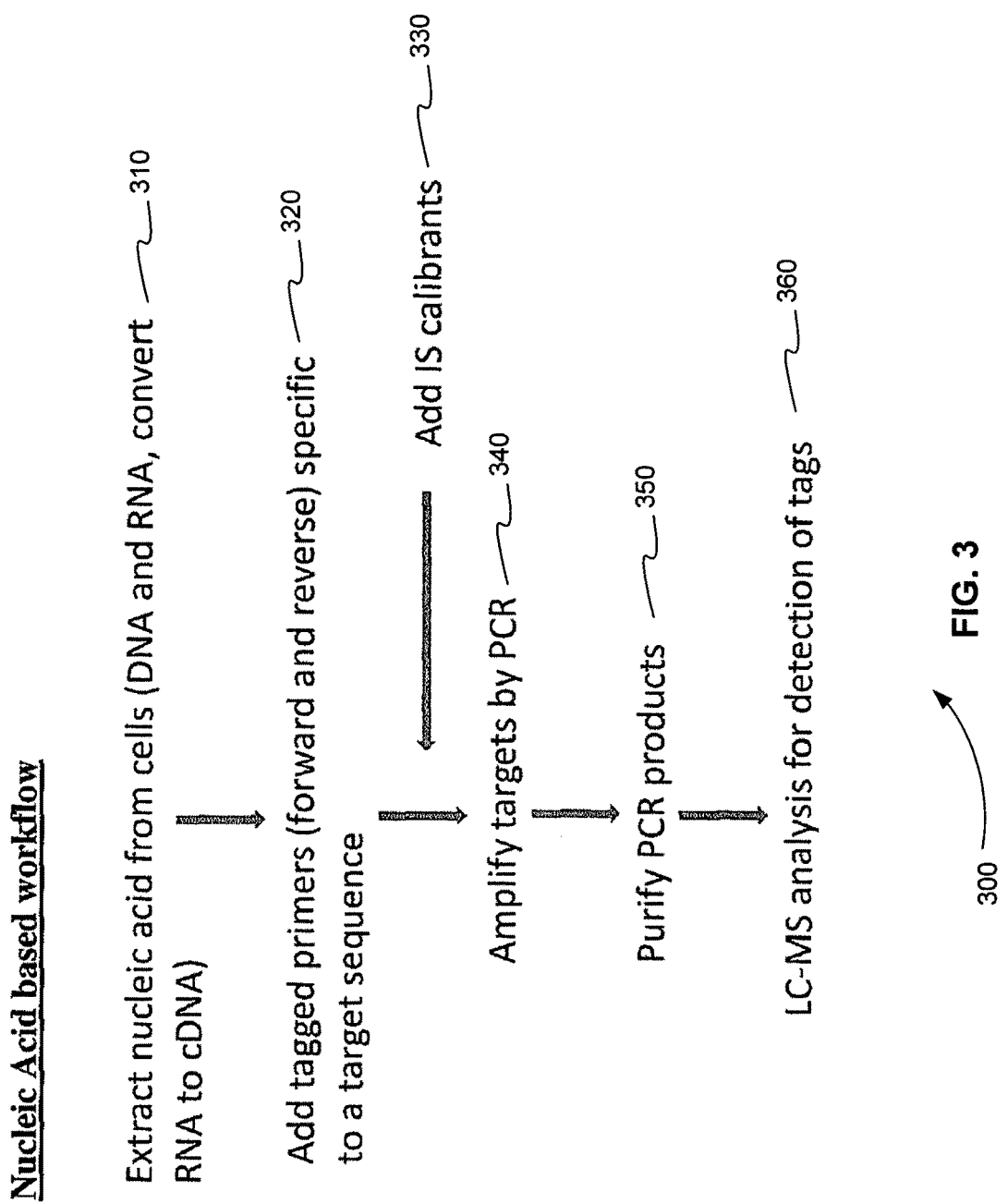
FIG. 3 is a flowchart showing an exemplary nucleic acid based workflow, in accordance with various embodiments.

FIG. 3 is a flowchart showing an exemplary nucleic acid based workflow 300, in accordance with various embodiments.

In step 310 of workflow 300, nucleic acid is extracted from cells.

In step 320, the nucleic acid is tagged with a first set of primer tags that bind to one or more target sequences of one or more known microbes.

In step 330, known sequences of the nucleic acid of one or more known microbes are determined on a computer, or in-silico, and the resulting sequences are synthesized. The synthesized known sequences are labeled with a second set of primer tags. Known quantities of one or more synthesized sequences are then added to the sample containing the nucleic acid tagged with a first set of primer tags.

In step 340, the target sequences and the synthesized sequences are amplified by PCR.

In step 350, the PCR products of target sequences and the synthesized sequences are purified.

In step 360, LC-MS analysis is performed on the PCR products. A microbe is identified by detecting one or more tags from the first set of primer tags. The microbe is further quantified by comparing the intensities of the one or more detected tags with the intensities of one or more tags from the second set of primer tags that identify the same microbe.

In various embodiments, methods and systems use uniquely designed tags similar to, for example, Amplifex™ Keto and Amplifex™ Diene tags from AB Sciex, but designed to react with amino terminal of peptides (e.g., N-hydroxysuccinimide (NHS) ester). The uniquely designed tags also have the properties of improving ionization efficiency of the tagged peptides thereby increasing signal intensity. As a result, detection of low abundance proteins can be achieved. Detection of the tags together with the sequence information in MSMS would provide for confirmatory identification of the peptide(s) and thereby the microbes of interest.

In various embodiments, the isotopic variants of the tags, such as isobaric, isomeric and mass differential, may be used for quantitation and multiplexing. By including isotopically coded internal standards of the peptides of interest, quantitation against the standard can be achieved.

In various embodiments, the tags are also designed to fragment in MS space without the need for photocleavage prior to introduction to a mass spectrometer. A workflow is designed to include tagged peptides unique to microbes of interest as internal standards. Peptides from the test sample are tagged with a pre-determined isotopic variant of the tag. Cleavage of the tags in MS and identification of the tag pair is used to identify the microbe in the test sample. This concept can also be used in a PCR based workflow where the specific primers are tagged.

Figure 4:
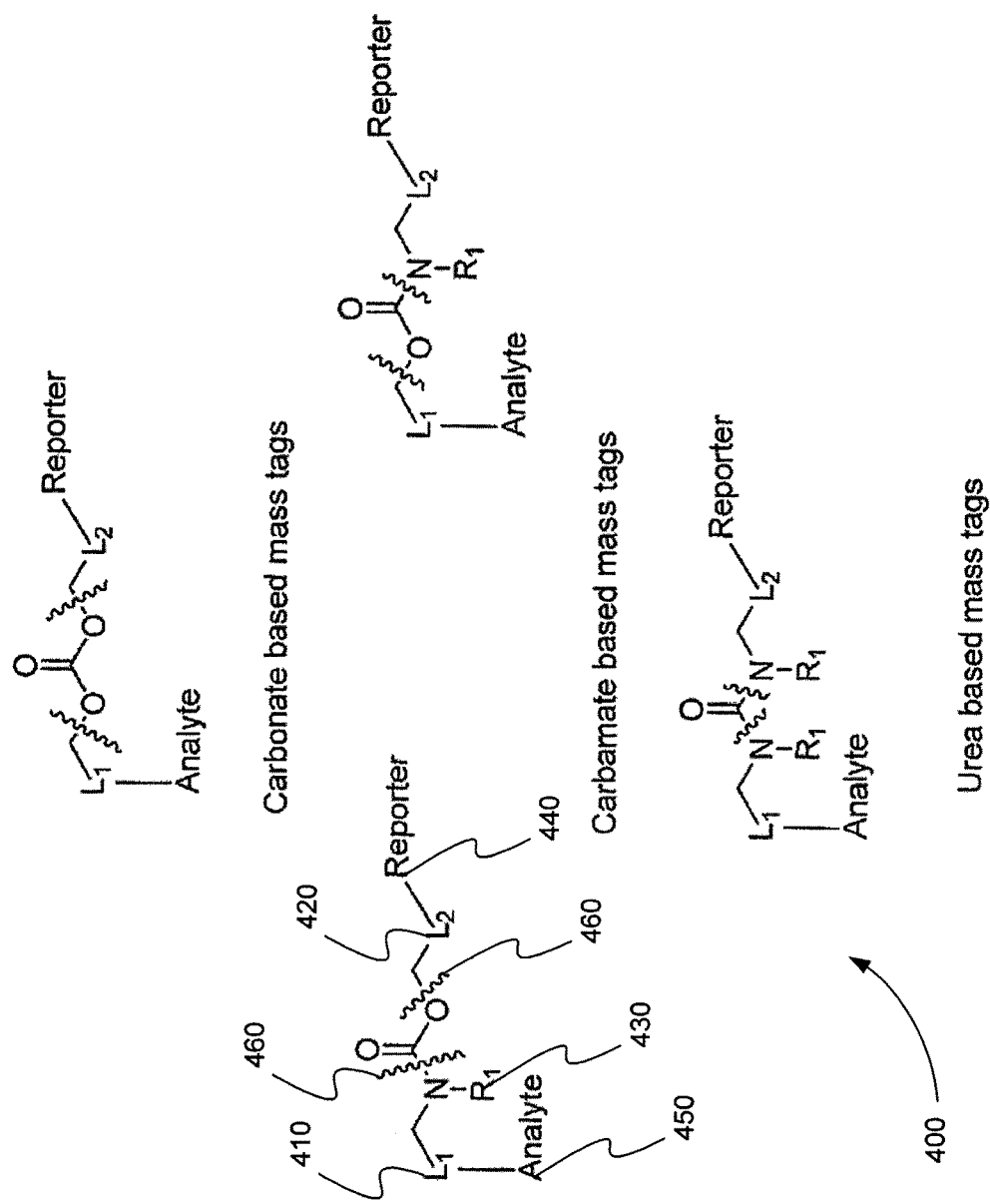
FIG. 4 is a diagram of four exemplary mass tags showing fragmentation modes, in accordance with various embodiments.

FIG. 4 is a diagram of four exemplary mass tags 400 showing fragmentation modes, in accordance with various embodiments. $L_1$ 410 and $L_2$ 420 are bonds or linkers. $R_1$ 430 is either H or a alkyl, alkyne, alkene, or aryl group, for example. A reporter 440 is a charged functional group. Non-limiting examples include triphenylmethyl (Ph3C), tialkylammonium (Me3N+), guanidinium, alkylated thio-ether (—S(Me)-Me+), and N-methylpyridinium. Analytes 450 can be conjugated to mass tags 400 via reacting with a reactive group on a linker, for example. Non-limiting examples of reactive groups are NHS ester, iodo-alkyl, dienophiles, aminoxy, and hydrazine. Fragmentation modes 460 can occur in the source, in Q1 of a quadrupole, or can be induced by a laser in MALDI instruments, for example.

In various embodiments, the tags are designed in such a way that there are multiple MS signal enhancing groups per tag. Upon fragmentation in the MS space all MS enhancing groups are released from the tag simultaneously.

Figure 5:
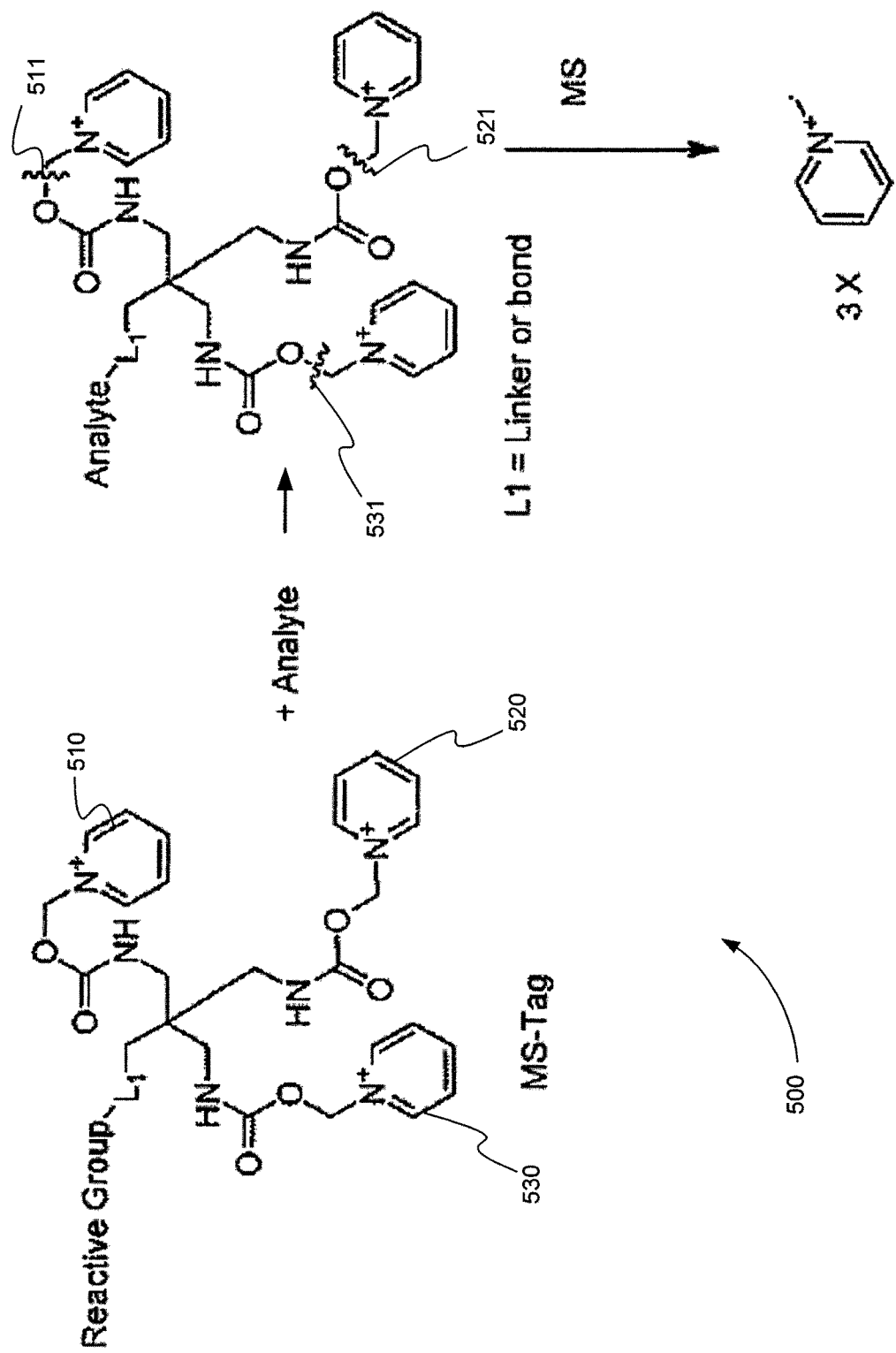
FIG. 5 is a diagram of an exemplary tag with multiple mass spectrometry (MS) signal enhancing groups, in accordance with various embodiments.

FIG. 5 is a diagram of an exemplary tag 500 with multiple MS signal enhancing groups, in accordance with various embodiments. Exemplary tag 500 includes MS signal enhancing groups 510, 520, and 530. MS signal enhancing groups 510, 520, and 530 are cleaved, for example, at locations 511, 521, and 531, respectively. The three MS signal enhancing groups 510, 520, and 530 provide three times the signal enhancement in addition to signal enhancement by the MS enhancing positively charged feature.

In various embodiments, these enhancing groups are the detection element. Simultaneous release of the MS enhancing groups amplifies the signal and lower the detection limit of the tagged analyte. These tags can be linked to the analyte via a secondary recognition element, such as (non-limiting) antibody or nano-particle, for example. These tags can also be covalently or non-covalently attached to a secondary recognition element directly or via a linker. One skilled in the art will appreciate that other types of connection methods can equally be used.

Figure 6:
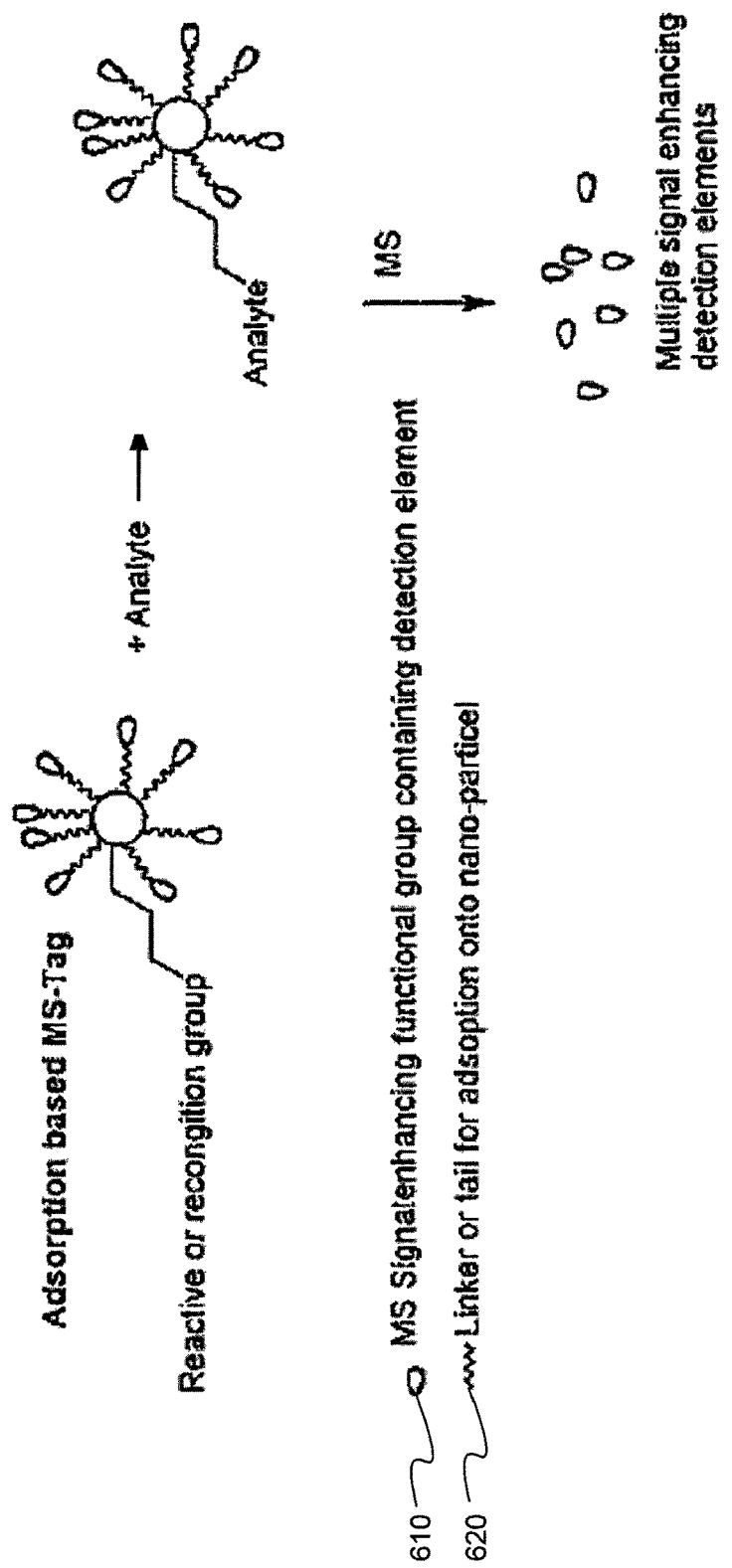
FIG. 6 is a diagram of an exemplary adsorption based tag with multiple signal enhancing detection elements, in accordance with various embodiments.

FIG. 6 is a diagram of an exemplary adsorption based tag 600 with multiple signal enhancing detection elements, in accordance with various embodiments. Tag 600 includes multiple MS signal enhancing detection elements 610 and linkers or tails for adsorption onto a nano-particle 620.

In various embodiments, pathogen-DNA is amplified by using rolling circle amplification. In such a case, whole or part of a rolling circle sequence can be complementary to an oligo-MS tag. After amplification, the system can be incubated with oligo-MS tag, followed by washing and MS analysis. Because of hybridization of multiple oligo-MS tag per amplified oligo, a signal can be enhanced many times. In various alternative embodiments, a MS-tag labeled nucleotide (e.g., labeled as deoxythymidine triphosphate (dTTP)) can be used during PCR amplification to produce the same effect.

In various embodiments, combinations of multiple MS signal enhancing group per tag plus rolling circle PCR can be used to further augment the amplification level.

Figure 7:
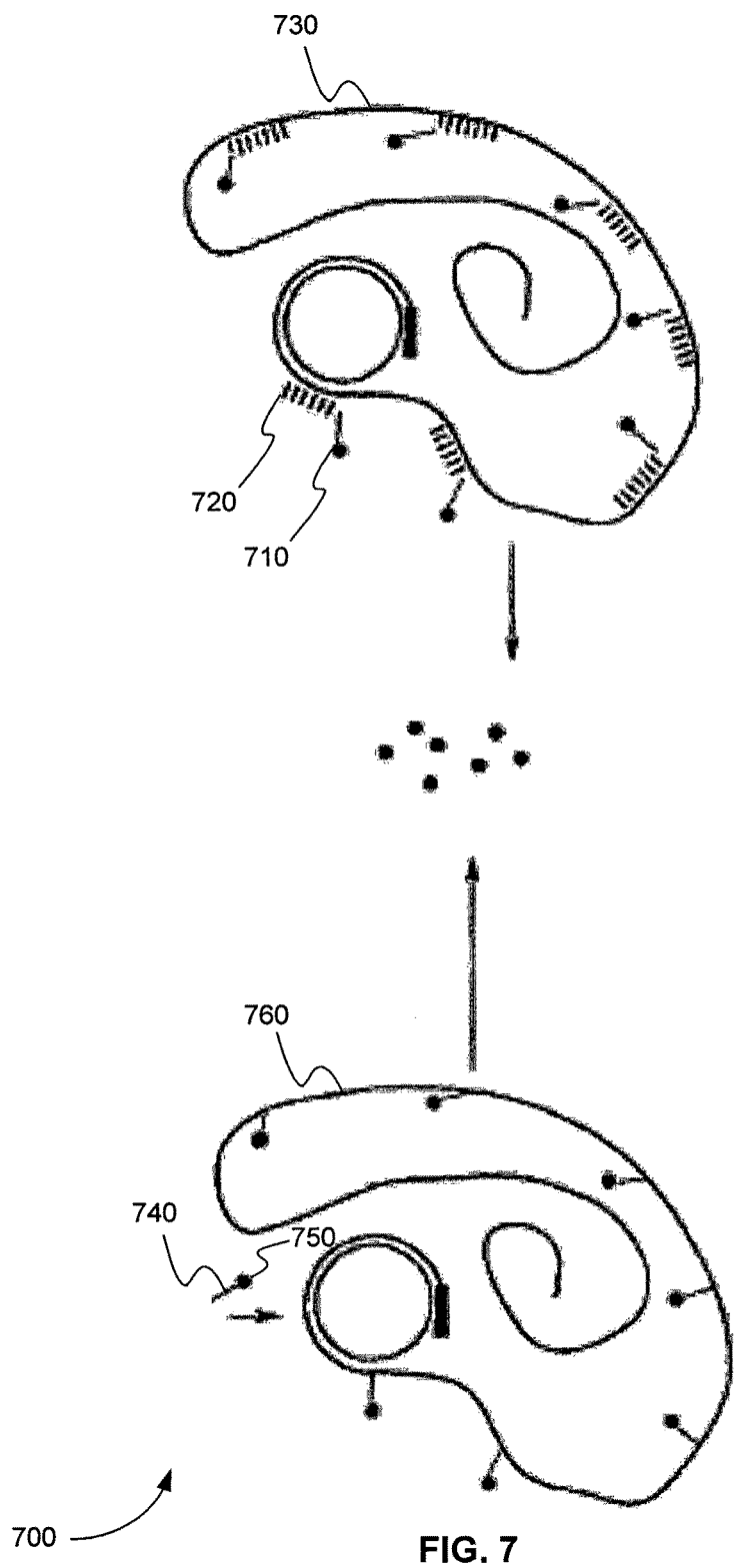
FIG. 7 is a diagram of signal amplification by a combination of rolling circle polymerase chain reaction (PCR) plus multiple MS signal enhancing detection elements, in accordance with various embodiments.

FIG. 7 is a diagram of signal amplification 700 by a combination of rolling circle PCR plus multiple MS signal enhancing detection elements, in accordance with various embodiments. Oligo-MS tags that include MS signal enhancing detection elements 710 and complementary sequences 720 are hybridized to part of the circular DNA of pathogen-DNA 730. In addition, PCR amplification can label nucleotides with tags 740 that bind MS signal enhancing detection elements 750 to pathogen-DNA 760. In both cases, the membrane is washed and MS analysis is performed. The detection of multiple MS signal enhancing detection elements per pathogen DNA then confirms the presence of the pathogen.

In summary, embodiments of methods and systems using MRM/SRM workflows offer specificity. The tag design improves sensitivity and no prior cleavage of tag is necessary. Internal standard allows for unambiguous identification and quantitative multiplexing.

System for Microbial Identification from Peptides

Figure 8:
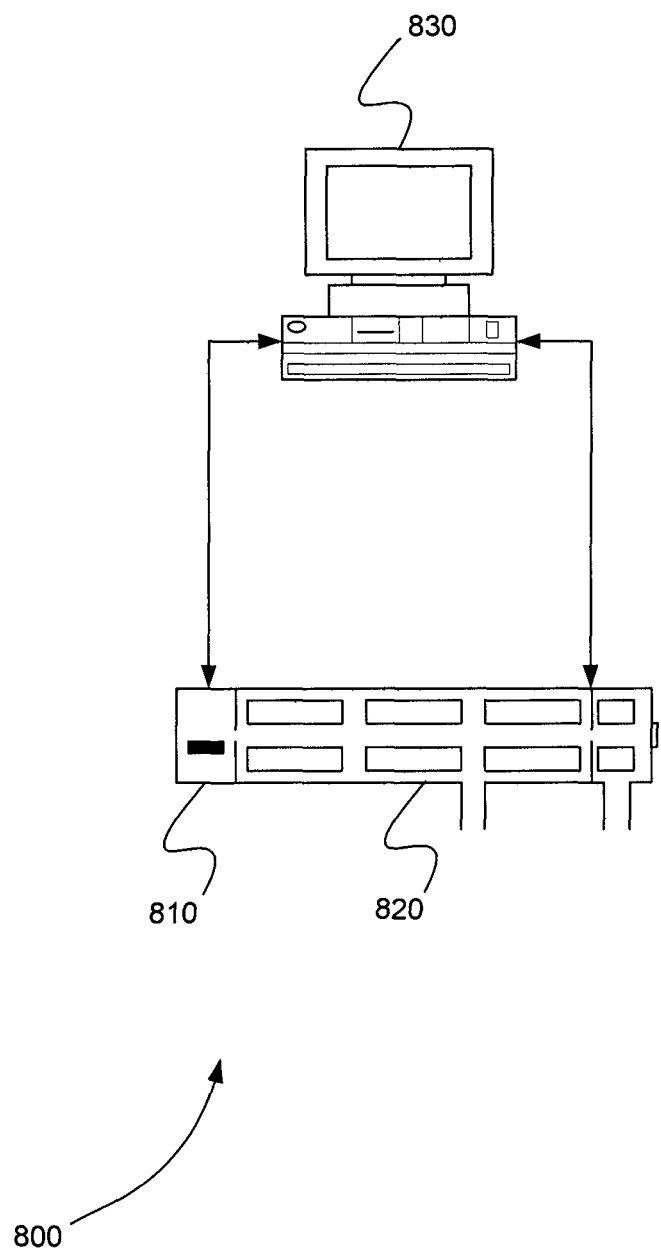
FIG. 8 is a schematic diagram showing a system for microbial identification using cleavable tags that bind to peptides, in accordance with various embodiments.

FIG. 8 is a schematic diagram showing a system 800 for microbial identification using cleavable tags that bind to peptides, in accordance with various embodiments. System 800 includes ion source 810, mass spectrometer 820, and processor 830. Ion source 810 provides a beam of ions from a sample. The sample includes peptides labeled with a first tag. The first tag binds to a peptide of a known microbe and is cleaved from the peptide of the known microbe during mass spectrometry. The first tag can be cleaved from the peptide of the known microbe in the ionization source, in Q1 of a triple quadrupole, or by a laser in a MALDI instrument, for example.

Mass spectrometer 820 can include one or more physical mass filters and one or more physical mass analyzers. A mass analyzer of a mass spectrometer can include, but is not limited to, a time-of-flight (TOF), quadrupole, an ion trap, a linear ion trap, an orbitrap, or a Fourier transform mass analyzer.

Mass spectrometer 820 can also include a separation device (not shown). The separation device can perform a separation technique that includes, but is not limited to, liquid chromatography, gas chromatography, capillary electrophoresis, or ion mobility. Mass spectrometer 820 can include separating mass spectrometry stages or steps in space or time, respectively. The separation device separates the sample from a mixture before the sample is ionized by ion source 810, for example.

Mass spectrometer 820 receives the beam of ions from ions source 810. Mass spectrometer 820 is adapted to perform an MRM method on the beam of ions.

Processor 830 can be, but is not limited to, a computer, microprocessor, or any device capable of sending and receiving control information and data to and from mass spectrometer 820 and processing data. Processor 830 is in communication with mass spectrometer 820 and ion source 810.

Processor 830 sends control information to mass spectrometer 820 to select the labeled peptide of the known microbe, fragment the labeled peptide of the known microbe, and monitor for an intensity of the first tag in the MRM method. If the intensity of the first tag received from mass spectrometer 820 exceeds a threshold value, processor 830 identifies the known microbe in the sample.

In various embodiments, the first tag is designed so that there are multiple enhancing groups per tag. In other words, the first tag includes two or more copies of a mass spectrometry enhancing group and the intensity of the first tag is an intensity of the mass spectrometry enhancing group.

In various embodiments, the first tag is linked to a peptide of the known microbe through a secondary recognition element. The secondary recognition element can include, but is not limited to, an antibody or a nano-particle.

In various embodiments, the identified microbe is also quantified using a known standard that is tagged with a second tag that is a variant of the first tag. For example, the sample further includes a known quantity of synthesized peptides of the known microbe labeled with a second tag. The second tag is also cleaved from the synthesized peptide of the known microbe during mass spectrometer. Processor 830 further sends control information to mass spectrometer 820 to also select the labeled synthesized peptide of the known microbe, fragment the labeled synthesized peptide of the known microbe, and monitor for an intensity of the second tag in the MRM method. Processor 830 calculates a quantity of the known microbe in the sample by comparing the measured intensity of the first tag and the measured intensity of the second tag.

Method for Microbial Identification from Peptides

Figure 9:
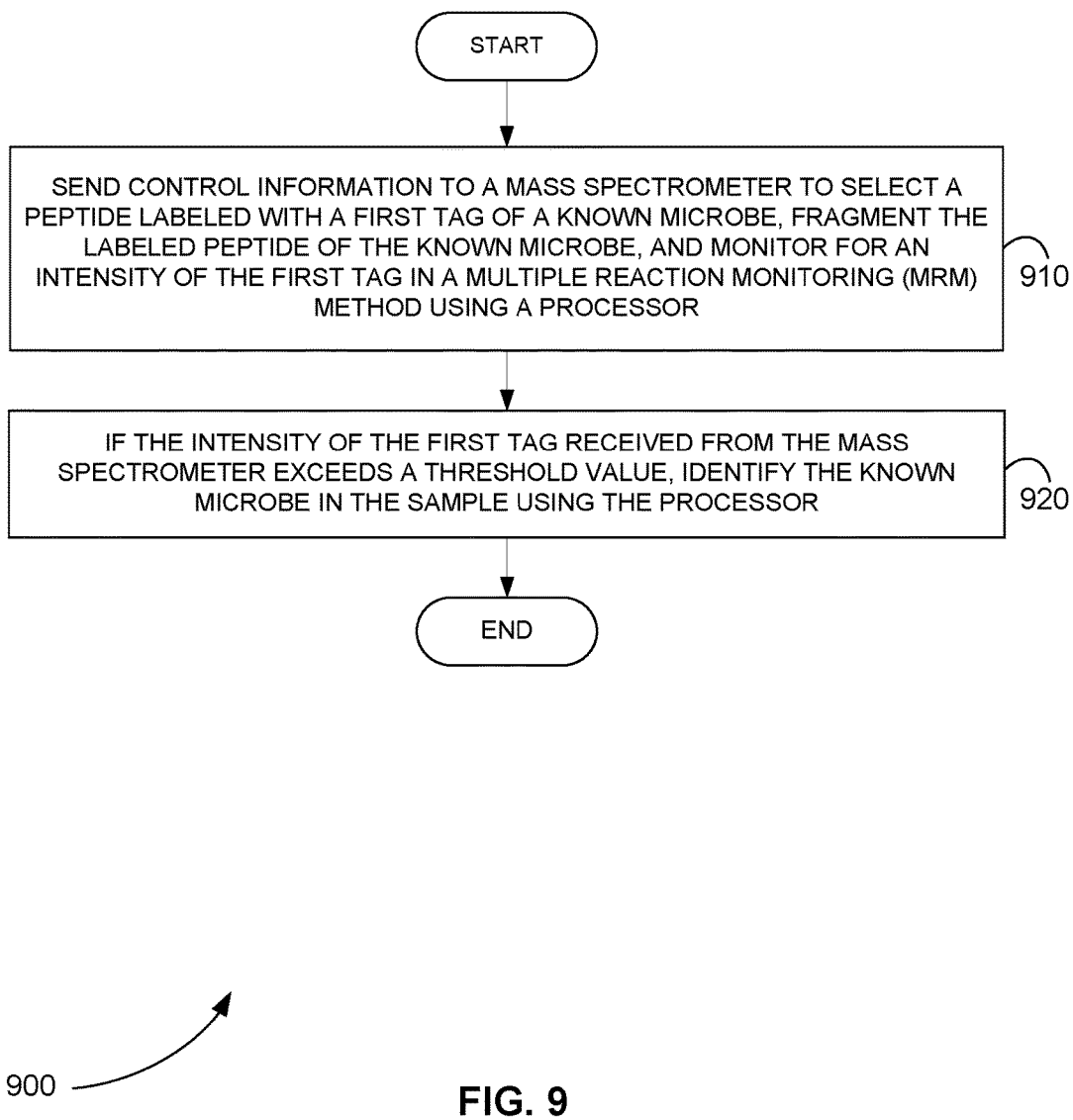
FIG. 9 is an exemplary flowchart showing a method for microbial identification using cleavable tags that bind to peptides, in accordance with various embodiments.

FIG. 9 is an exemplary flowchart showing a method 900 for microbial identification using cleavable tags that bind to peptides, in accordance with various embodiments.

In step 910 of method 900, control information is sent to a mass spectrometer to select a peptide labeled with a first tag of a known microbe, fragment the labeled peptide of the known microbe, and monitor for an intensity of the first tag in an MRM method using a processor. An ion source provides a beam of ions from a sample that includes peptides labeled with the first tag. The first tag binds to a peptide of a known microbe and is cleaved from the peptide of the known microbe during mass spectrometry. The mass spectrometer receives the beam of ions and is adapted to perform the MRM method on the beam of ions.

In step 920, if the intensity of the first tag received from the mass spectrometer exceeds a threshold value, the known microbe is identified in the sample using the processor.

Computer Program Product for Microbial Identification from Peptides

In various embodiments, computer program products include a tangible computer-readable storage medium whose contents include a program with instructions being executed on a processor so as to perform a method for microbial identification using cleavable tags that bind to peptides. This method is performed by a system that includes one or more distinct software modules.

Figure 10:
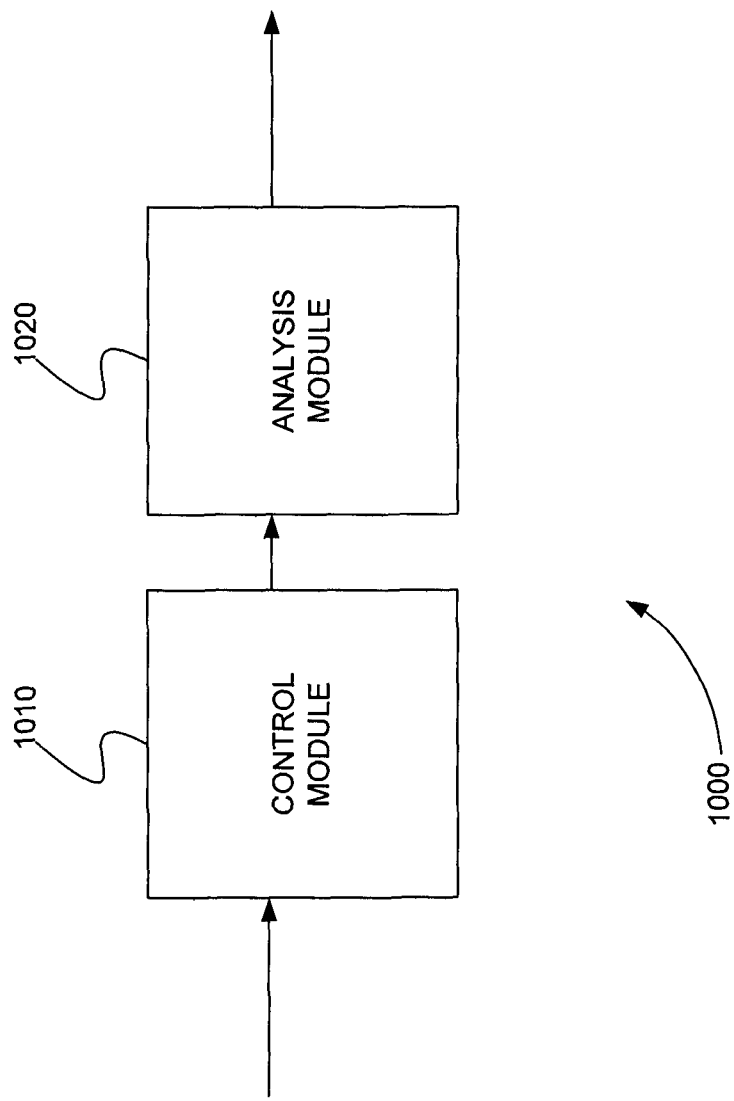
FIG. 10 is a schematic diagram of a system that includes one or more distinct software modules that performs a method for microbial identification using cleavable tags that bind to peptides, in accordance with various embodiments.

FIG. 10 is a schematic diagram of a system 1000 that includes one or more distinct software modules that performs a method for microbial identification using cleavable tags that bind to peptides, in accordance with various embodiments. System 1000 includes control module 1010 and analysis module 1020.

Control module 1010 sends control information to a mass spectrometer to select a peptide labeled with a first tag of a known microbe, fragment the labeled peptide of the known microbe and monitor for an intensity of the first tag in an MRM method. An ion source provides a beam of ions from a sample that includes peptides labeled with the first tag. The first tag binds to a peptide of a known microbe. The first tag is cleaved from the peptide of the known microbe during mass spectrometry. The mass spectrometer receives the beam of ions and is adapted to perform the MRM method on the beam of ions.

If the intensity of the first tag received from the mass spectrometer exceeds a threshold value, analysis module 1020 identifies the known microbe in the sample.

System for Microbial Identification from Nucleic Acids

Returning to FIG. 8, system 800 can also be used for microbial identification using cleavable tags that bind to nucleic acids, in accordance with various embodiments. Ion source 810 provides a beam of ions from a polymerase chain reaction (PCR) amplified sample. The sample includes one or more nucleic acid primers labeled with a first tag. The first tag binds to one or more nucleic acid primers of a known microbe. The first tag is cleaved from the one or more nucleic acid primers of the known microbe during mass spectrometry.

Mass spectrometer 820 receives the beam of ions from ion source 810. Mass spectrometer 820 is adapted to perform an MS method on the beam of ions.

Processor 830 sends control information to mass spectrometer 820 to fragment the labeled one or more nucleic acid primers and monitor for an intensity of the first tag in the MS method. If the intensity of the first tag received from mass spectrometer 820 exceeds a threshold value, processor 830 identifies the known microbe in the sample.

In various embodiments, the first tag includes two or more copies of a mass spectrometry enhancing group and the intensity of the first tag is an intensity of the mass spectrometry enhancing group.

In various embodiments, the first tag is linked to a nucleic acid of the known microbe through a secondary recognition element. The secondary recognition element can include, but is not limited to, an antibody or a nano-particle.

In various embodiments, the identified microbe can be quantified. For example, the sample further includes a known quantity of one or more synthesized nucleic acid primers of the known microbe labeled with a second tag. The second tag is cleaved from the one or more synthesized nucleic acid primers of the known microbe during mass spectrometry. Processor 830 further sends control information to mass spectrometer 820 to fragment the labeled one or more synthesized nucleic acid primers of the known microbe and monitor for an intensity of the second tag in the MS method. Processor 830 calculates a quantity of the known microbe in the sample by comparing the intensity of the first tag and the intensity of the second tag.

Method for Microbial Identification from Nucleic Acids

Figure 11:
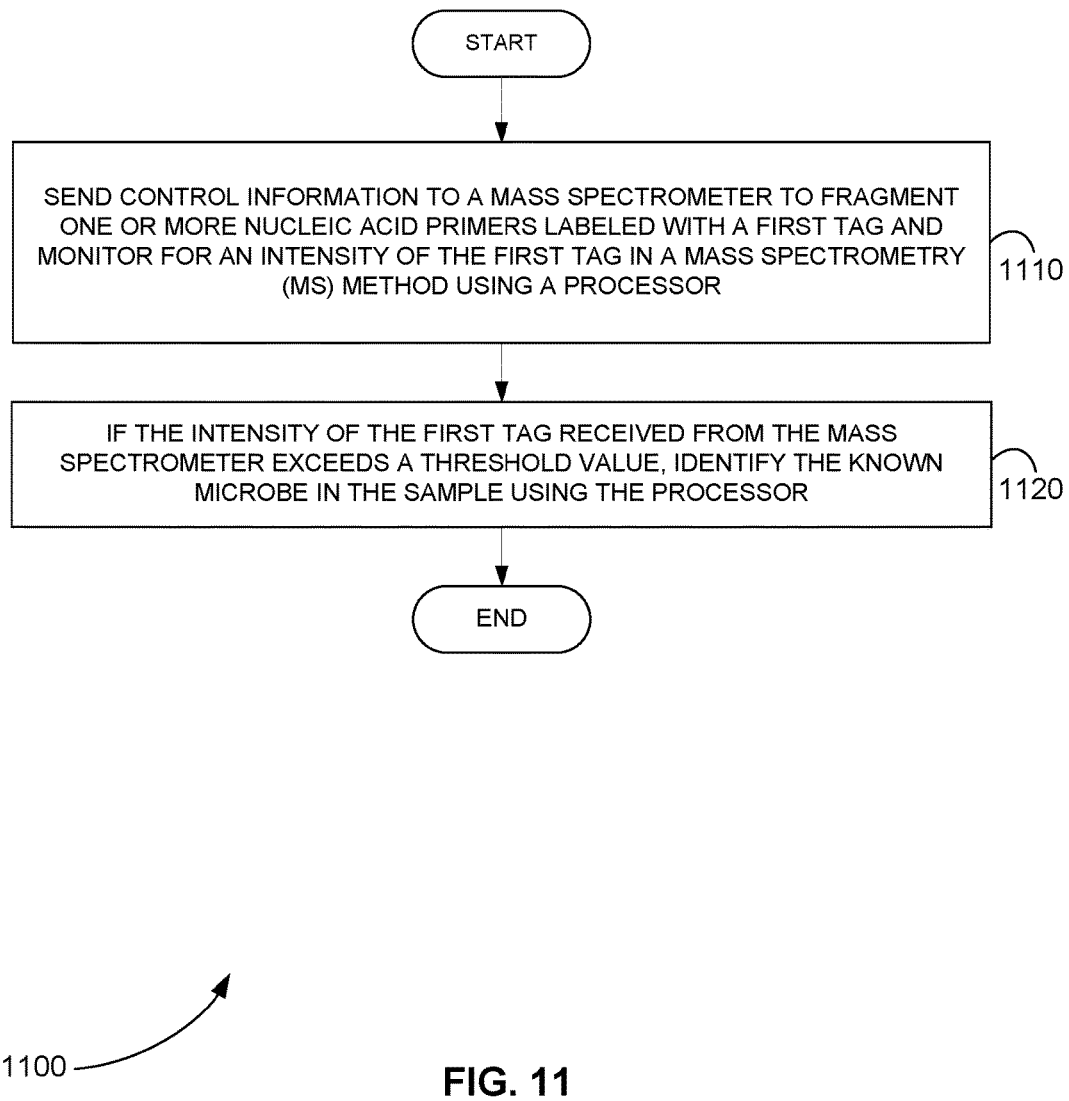
FIG. 11 is an exemplary flowchart showing a method for microbial identification using cleavable tags that bind to nucleic acids, in accordance with various embodiments.

FIG. 11 is an exemplary flowchart showing a method 1100 for microbial identification using cleavable tags that bind to nucleic acids, in accordance with various embodiments.

In step 1110 of method 1100, control information is sent to a mass spectrometer to fragment one or more nucleic acid primers labeled with a first tag and monitor for an intensity of the first tag in an MS method using a processor. An ion source provides a beam of ions from a PCR amplified sample. The sample includes one or more nucleic acid primers labeled with the first tag. The first tag binds to one or more nucleic acid primers of a known microbe. The first tag is cleaved from the one or more nucleic acid primers of the known microbe during the MS method. The mass spectrometer receives the beam of ions from the ions source and is adapted to perform the MS method on the beam of ions.

In step 1120, if the intensity of the first tag received from the mass spectrometer exceeds a threshold value, the known microbe is identified in the sample using the processor.

Computer Program Product for Microbial Identification from Nucleic Acids

In various embodiments, computer program products include a tangible computer-readable storage medium whose contents include a program with instructions being executed on a processor so as to perform a method for microbial identification using cleavable tags that bind to nucleic acids. This method is performed by a system that includes one or more distinct software modules.

Returning to FIG. 10, system 1000 can also be used to perform a method for microbial identification using cleavable tags that bind to nucleic acids, in accordance with various embodiments. Control module 1010 sends control information to a mass spectrometer to fragment one or more nucleic acid primers labeled with a first tag and monitor for an intensity of the first tag in an MS method. An ion source provides a beam of ions from a PCR amplified sample that includes one or more nucleic acid primers labeled with the first tag. The first tag binds to one or more nucleic acid primers of a known microbe. The first tag is cleaved from the one or more nucleic acid primers of the known microbe during the MS method. The mass spectrometer receives the beam of ions from the ion source and is adapted to perform the MS method on the beam of ions.

If the intensity of the first tag received from the mass spectrometer exceeds a threshold value, analysis module 1020 identifies the known microbe in the sample.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for microbial identification using cleavable tags that bind to peptides, comprising:
    an ion source that provides a beam of ions from a sample that includes peptides labeled with a first tag that binds to a peptide of a known microbe and is cleaved from the peptide of the known microbe during mass spectrometry;
    a mass spectrometer that receives the beam of ions and is adapted to perform a multiple reaction monitoring (MRM) method on the beam of ions; and
    a processor in communication with the mass spectrometer and the ion source that
        sends control information to the mass spectrometer to select the labeled peptide of the known microbe, fragment the labeled peptide of the known microbe, and monitor for the first tag in the MRM method, and
        if an intensity of the first tag received from the mass spectrometer exceeds a threshold value, identifies the known microbe in the sample, wherein the first tag includes two or more copies of a mass spectrometry enhancing group that increase the intensity of the mass spectrometry enhancing group two or more times when the labeled peptide is fragmented to increase a signal intensity and lower a detection limit of the known microbe, wherein the mass spectrometer monitors for the mass spectrometry enhancing group, and wherein the intensity of the first tag is an intensity of the mass spectrometry enhancing group.

2. The system of claim 1, wherein the first tag is linked to a peptide of the known microbe through a secondary recognition element.

3. The system of claim 2, wherein the secondary recognition element comprises an antibody or a nano-particle.

4. The system of claim 1, wherein the sample further includes a known quantity of synthesized peptides of the known microbe labeled with a second tag that is cleaved from the synthesized peptide of the known microbe during mass spectrometry, and wherein the processor further
    sends control information to the mass spectrometer to also select the labeled synthesized peptide of the known microbe, fragment the labeled synthesized peptide of the known microbe, and monitor for the second tag in the MRM method, and
    calculates a quantity of the known microbe in the sample by comparing the intensity of the first tag and an intensity of the second tag.

5. A method for microbial identification using cleavable tags that bind to peptides, comprising:

sending control information to a mass spectrometer to select a peptide labeled with a first tag of a known microbe, fragment the labeled peptide of the known microbe, and monitor for the first tag in a multiple reaction monitoring (MRM) method using a processor, wherein an ion source provides a beam of ions from a sample that includes peptides labeled with the first tag, wherein the first tag binds to a peptide of a known microbe and is cleaved from the peptide of the known microbe during mass spectrometry, and wherein the mass spectrometer receives the beam of ions and is adapted to perform the MRM method on the beam of ions; and if an intensity of the first tag received from the mass spectrometer exceeds a threshold value, identifying the known microbe in the sample using the processor, wherein the first tag includes two or more copies of a mass spectrometry enhancing group that increase the intensity of the mass spectrometry enhancing group two or more times when the labeled peptide is fragmented to increase a signal intensity and lower a detection limit of the known microbe, wherein the mass spectrometer monitors for the mass spectrometry enhancing group, and wherein the intensity of the first tag is an intensity of the mass spectrometry enhancing group.

6. The method of claim 5, wherein the first tag is linked to a peptide of the known microbe through a secondary recognition element.

7. The method of claim 5, wherein the sample further includes a known quantity of synthesized peptides of the known microbe labeled with a second tag that is cleaved from the synthesized peptide of the known microbe during mass spectrometry, and further comprising:

sending control information to the mass spectrometer to also select the labeled synthesized peptide of the known microbe, fragment the labeled synthesized peptide of the known microbe, and monitor for the second tag in the MRM method using the processor, and calculating a quantity of the known microbe in the sample by comparing the intensity of the first tag and an intensity of the second tag using the processor.

* * * * *